(12) United States Patent
Gradon et al.

(10) Patent No.: US 6,832,610 B2
(45) Date of Patent: Dec. 21, 2004

(54) BREATHING ASSISTANCE APPARATUS

(75) Inventors: Lewis George Gradon, Auckland (NZ); Alastair Edwin McAuley, Auckland (NZ); Chris Earl Nightingale, Auckland (NZ); Ivan Milivojevic, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/268,870

(22) Filed: Oct. 10, 2002

(65) Prior Publication Data

US 2003/0066531 A1 Apr. 10, 2003

(30) Foreign Application Priority Data

Oct. 10, 2001 (NZ) ................................. 514750
Jun. 12, 2002 (NZ) ................................. 519541

(51) Int. Cl.[7] ............................................. A62B 18/08
(52) U.S. Cl. ............................... 128/206.27; 128/206.24
(58) Field of Search ................. 128/201.22–201.25, 128/201.28, 205.25, 205.27, 205.28, 206.12–206.15, 206.17–206.19, 206.21, 206.24, 206.25, 206.26–206.28, 207.11, 207.12, 207.13, 200.28, DIG. 26, 912; 2/DIG. 11, 9, 411, 414, 424, 425; D24/110.5, 110.1

(56) References Cited

U.S. PATENT DOCUMENTS

| | | | |
|---|---|---|---|
| 4,919,128 A | * 4/1990 | Kopala et al. | 128/207.18 |
| 5,042,478 A | * 8/1991 | Kopala et al. | 128/207.18 |
| 5,243,971 A | 9/1993 | Sullivan et al. | |
| 5,542,128 A | 8/1996 | Lomas | |
| 5,570,689 A | 11/1996 | Starr et al. | |
| 6,112,746 A | 9/2000 | Kwok et al. | |
| 6,119,693 A | * 9/2000 | Kwok et al. | 128/207.11 |
| D439,326 S | * 3/2001 | Hecker et al. | D24/110.5 |
| 6,427,694 B1 | 8/2002 | Hecker et al. | |
| 6,435,181 B1 | 8/2002 | Jones, Jr. et al. | |
| 6,467,483 B1 | * 10/2002 | Kopacko et al. | 128/207.12 |
| 6,494,207 B1 | 12/2002 | Kwok | |
| 6,513,526 B2 | 2/2003 | Kwok et al. | |
| 6,520,182 B1 | 2/2003 | Gunaratnam | |
| 6,532,961 B1 | * 3/2003 | Kwok et al. | 128/206.21 |
| 6,557,556 B2 | * 5/2003 | Kwok et al. | 128/207.11 |
| 6,581,594 B1 | 6/2003 | Drew et al. | |
| 6,595,214 B1 | * 7/2003 | Hecker et al. | 128/207.13 |

FOREIGN PATENT DOCUMENTS

| | | |
|---|---|---|
| WO | WO 0057942 | 10/2000 |
| WO | WO 0078384 | 12/2000 |
| WO | WO 0100266 | 1/2001 |

* cited by examiner

Primary Examiner—Teena Kay Mitchell
(74) Attorney, Agent, or Firm—Trexler, Bushnell, Giangiorgi, Blackstone & Marr, Ltd.

(57) ABSTRACT

A patient interface for CPAP is described, with deformable cushions for the forehead rest. Each cushion providing a substantially even load bearing surface and progressive deformation. Several embodiments are disclosed for achieving desired mode(s) of deformation.

8 Claims, 7 Drawing Sheets

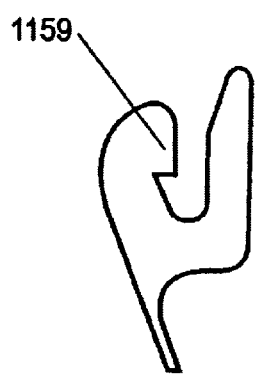
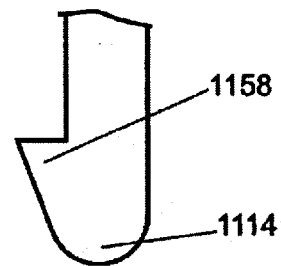
FIGURE 5  FIGURE 6
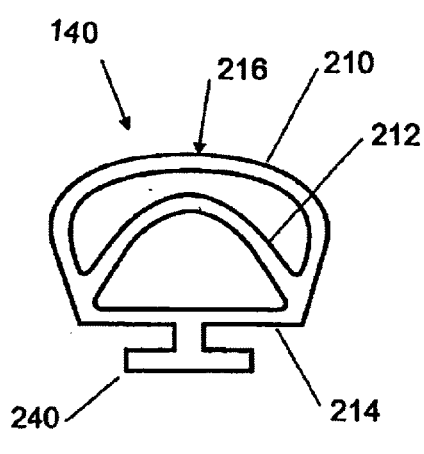
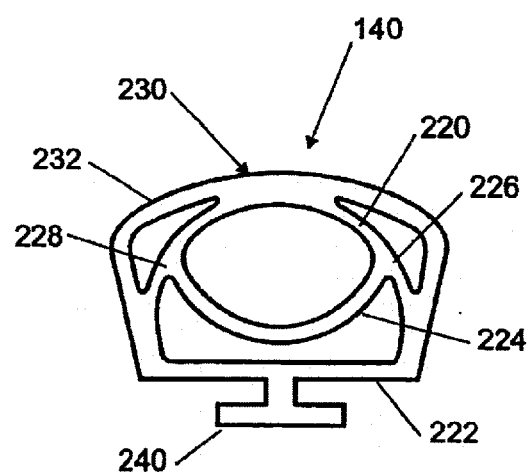
FIGURE 8  FIGURE 10

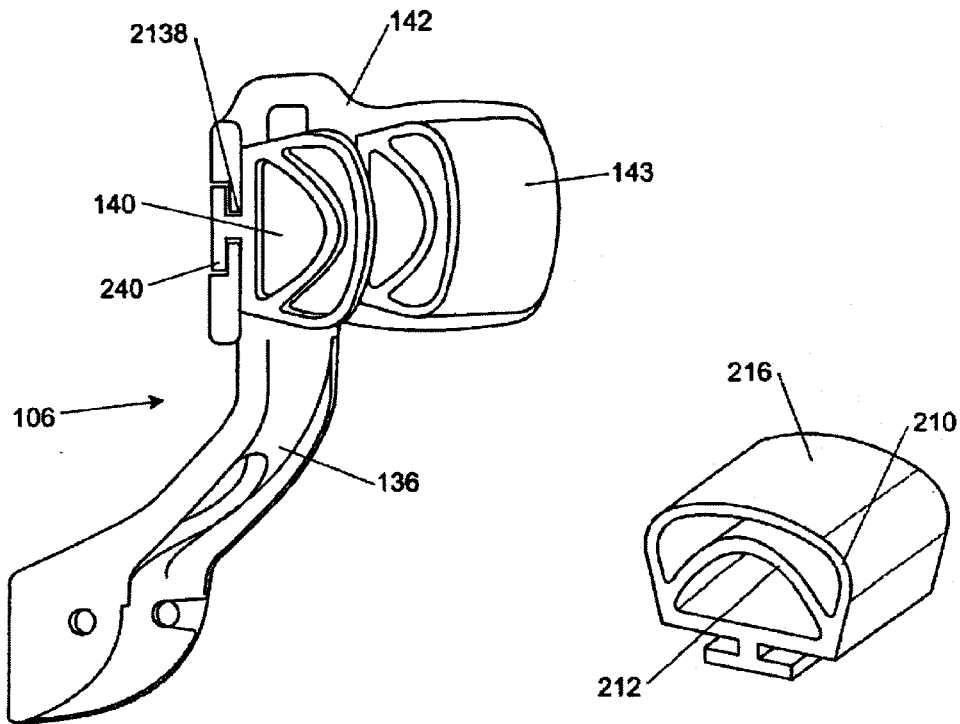
FIGURE 7          FIGURE 9
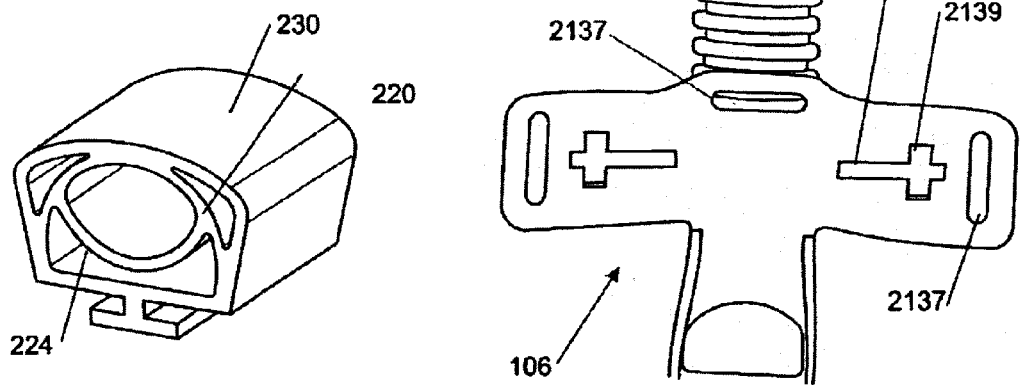
FIGURE 11          FIGURE 12

BREATHING ASSISTANCE APPARATUS

FIELD OF INVENTION

This invention relates to patient interfaces particularly though not solely for use in delivering CPAP therapy to patients suffering from obstructive sleep apnoea (OSA).

BACKGROUND OF THE INVENTION

In the art of respiration devices, there are well known variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. Nos. 5,243,971 and U.S. Pat. No. 6,112,746 are examples of prior art attempts to improve the mask system. U.S. Pat. No. 5,570,689 and PCT publication No. WO 00/78384, and U.S. Pat. No. 6,119,693 are examples of attempts to improve the forehead rest.

SUMMARY OF THE INVENTION

It is an object of the present invention to attempt to provide a patient interface which goes some way to overcoming the abovementioned disadvantages in the prior art or which will at least provide the industry with a useful choice.

Accordingly in one aspect the present invention may broadly be said to consist in a device for delivering a supply of gases to a user comprising:

a patient interface, in use in fluid communication with said supply of gases, a forehead rest engaging said interface including a deformable resilient member configured to in Use rest against the face of a user, said deformable resilient member including curved portion and a section curved portion.

Preferably said deformable resilient member is configured to provide at least a first mode of deformation and a second mode of deformation, where in the force required to deform in said first mode is less than that required to deform in said second mode.

Preferably said deformable resilient member includes a load bearing surface is adapted to provide a substantially even deforming force.

Preferably said first mode of deformation comprises said first curved portion deforming and said second mode of deformation comprises the composite deforming of said first curved portion and said second curved portion.

Preferably said second curved portion is nested within, and similar to cross sectional shape to said first curved portion.

Preferably said second curved member is smaller in cross section than said first curved member and either or both are attached at each end to a base member.

Preferably a first curved portion is attached at both ends to a base member and said second curved portion is inverted and attached at each end to, and smaller in height than, said first curved member; said second mode of deformation begins where said second bridge member is in contact with said base member and both said first bridge member and said second bridge member simultaneously deform.

Preferably said first bridge further comprises further members attaching to the said curved section at least three points to form an outer cross section substantially quadrilateral in cross section.

Preferably said resilient deformable member is moulded from silicon.

Preferably said resilient deformable member is extruded from silicon.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which;

FIG. 5 is a cutaway view of the periphery of the outer membrane, FIG. 6 is a cutaway view of the periphery of the mask body portion, FIG. 7 shows the forehead rest in isolation, FIG. 8 shows a section view of a forehead rest cushion.

FIG. 9 shows a perspective view of a forehead rest cushion,

FIG. 10 is a section of a further forehead rest cushion,

FIG. 11 is a section of perspective view of a further forehead rest cushion and

FIG. 12 is a back view showing the slots for each cushion to lock into.

Referring now to FIGS. 3 and 4 in particular, the mask cushion 1104 is provided around the periphery of the nasal mask 1102 to provide an effective seal onto the face of the user to prevent leakage. The mask cushion 1104 is shaped to approximately follow the contours of a patient's face. The mask cushion 1104 will deform when pressure is applied by the headgear (not shown, but similar to the headgear 108 shown in FIG. 2) to adapt to the individual contours of any particular user. In particular, there is an indented section 1150 intended to fit over the bridge of the user's nose as well as a less indented section 1152 to seal around the section beneath the nose and above the upper lip.

DETAILED DESCRIPTION

The present invention provides improvements in the delivery of CAP therapy. In particular a patient interface is described which is quieter for the user to wear and reduces the side leakage as compared with the prior art. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks, oral masks and mouthpieces.

Figure 1:
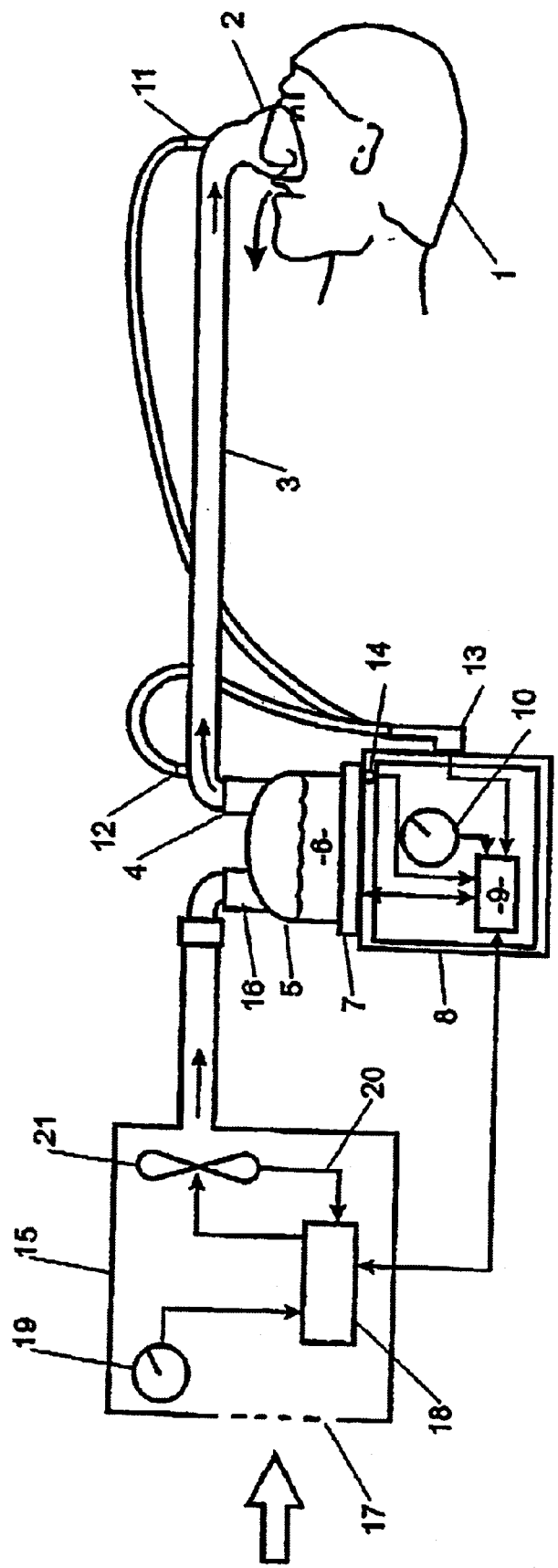
FIG. 1 is a block diagram of a humidified continuous positive airway pressure (system) as might be used in conjunction with the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. in response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 2:
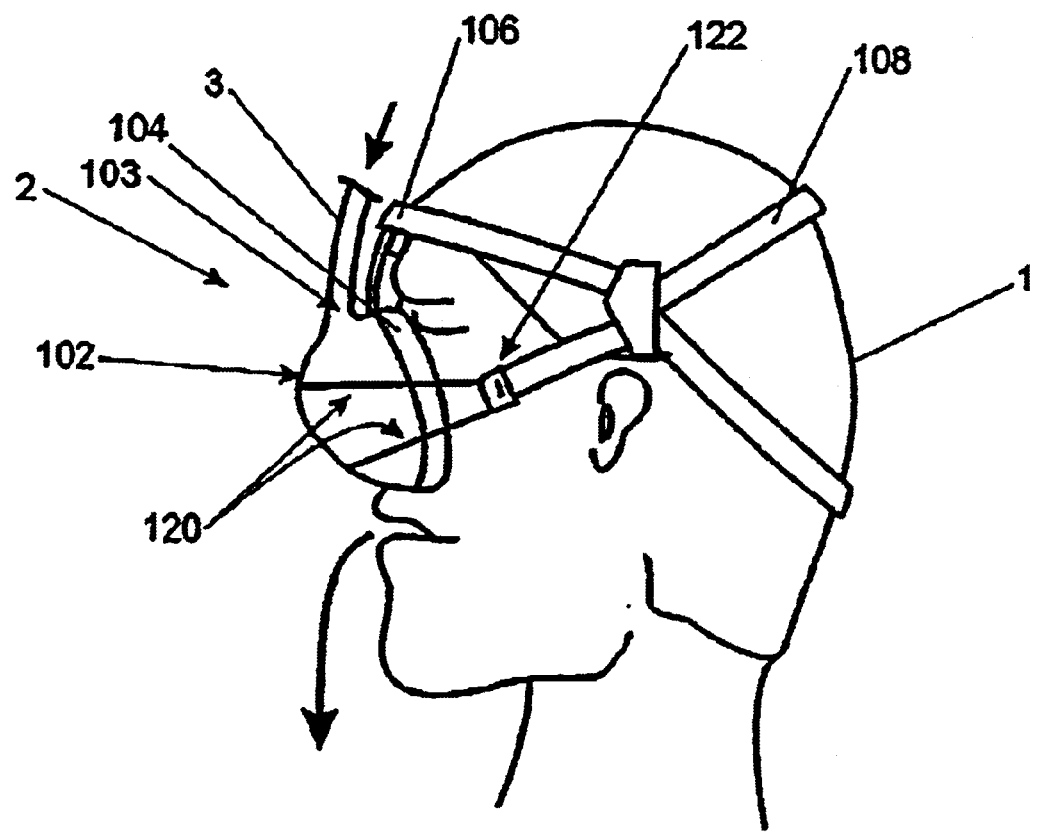
FIG. 2 is an illustration of the nasal mask in use according to the preferred embodiment of the present invention.

According to a first embodiment of the present invention the patient interface is shown in FIG. 2 as a mask. It will be appreciated the patient interface could equally be a nasal mask, full face, oral mask or mouth piece, endotracheal tube or cannula by way of example. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
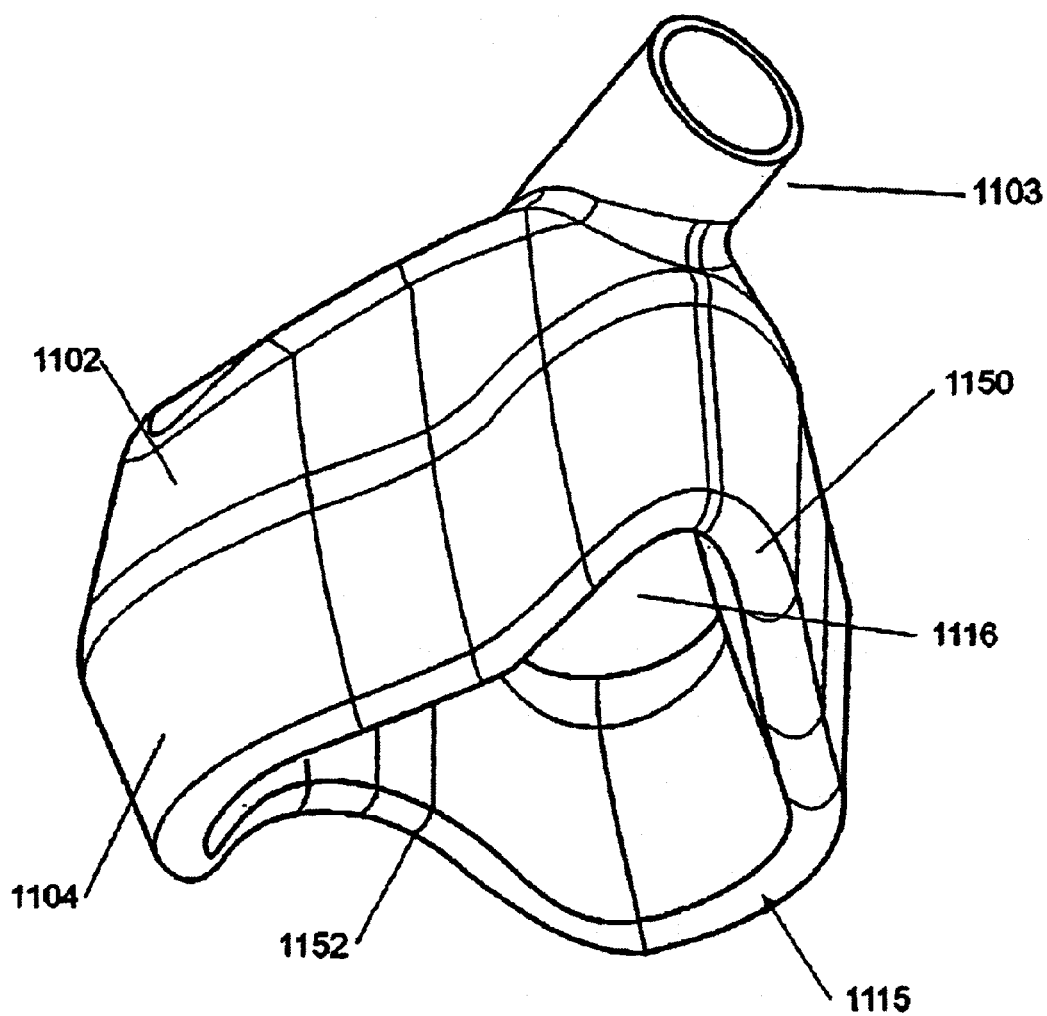
FIG. 3 shows a perspective view of the mask with cushion.
Figure 4:
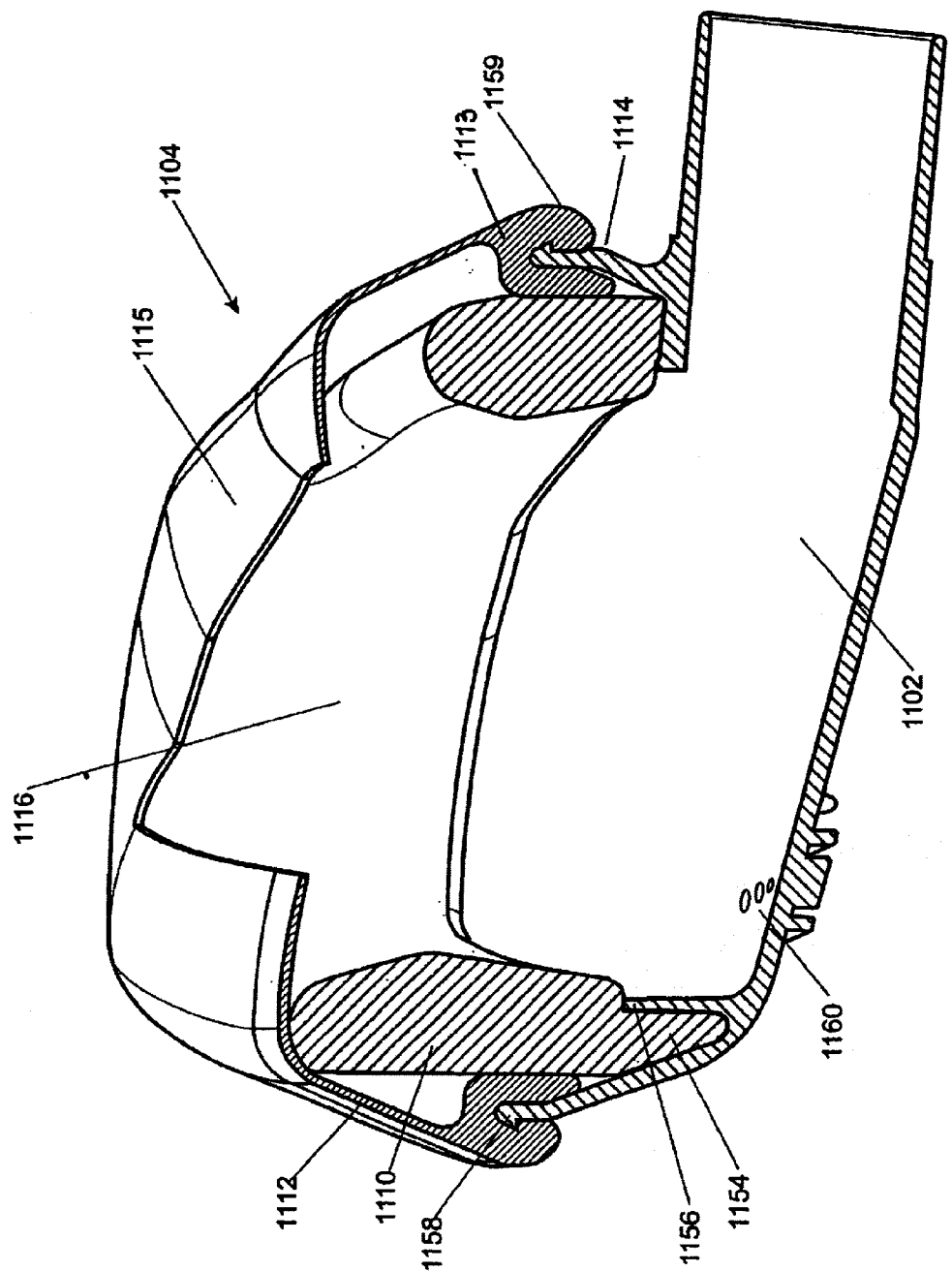
FIG. 4 is a cutaway view of the mask showing the cushion.

Referring now to FIGS. 3 and 4 in particular, the mask cushion 1104 is provided around the periphery of the nasal mask 1102 to provide an effective seal onto the face of the user to prevent leakage. The mask cushion 1104 is shaped to approximately follow the contours of a patient's face. The mask cushion 1104 will deform when pressure is applied by the headgear 1108 to adapt to the individual contours of any particular user. In particular, there is an indented section 1150 intended to fit over the bridge of the user's nose as well as a less indented section 1152 to seal around the section beneath the nose and above the upper lip.

In FIG. 4 we see that the mask cushion 1104 is composed of a inner foam cushion 1110 covered by an outer sealing sheath 1112. The inner cushion 1110 is constructed of a resilient material for example polyurethane foam, to distribute the pressure evenly along the seal around the user's face. The inner cushion 1110 is located around the outer periphery 1114 of the open face 1116 of the hollow body 1102. Similarly the outer sheath 1112 may be commonly attached at its base 1113 to the periphery 1114 and loosely covers over the top of the inner cushion 1110.

In the preferred embodiment shown in FIGS. 3–6 the bottom of the inner cushion 1110 fits into a generally triangular cavity 1154 in the hollow body 1102. The cavity 1154 is formed from a flange 1156 running mid-way around the interior of the hollow body.

The outer sheath 1112 fits in place over the cushion 1110, holding it in place. The sheath 1112 is secured by a snap-fit to the periphery 1114 of the hollow body. In FIGS. 5–6 the periphery 1114 is shown including an outer bead 158. The sheath 1112 includes a matching bead 1159, whereby once stretched around the periphery, the two beads engage to hold the sheath in place.

Forehead Rest

In the preferred embodiment of the present invention the nasal mask 102 includes a forehead rest 106 (seen in FIGS. 2 and 7). In one variation the attachment of the forehead rest 106 to the hollow body 102 effectively allows the forehead rest 106 to move freely in proximity to the user but with no lateral movement. Alternatively it may be permanently fixed or adjustably fixed.

At the top end 142 (around the user's forehead) of the bridge member 136 harnessing slots (not shown, but similar to those slots 2137 as shown in FIG. 12) are provided which allow straps from the headgear to be inserted to secure the mask to the headgear. For the user's comfort one or more resilient cushions 140 are provided on the T section at 142 the top end of the bridge member 136, to rest on the forehead of the user. The cushion 140 might be constructed eg. injection marbled or extruded, from silicon or any foam materials as is known in the art for providing cushioning. In FIG. 7 a second cushion 143 is shown at the other end of the section 142.

Forehead Rest Cushion

Figure 8A:
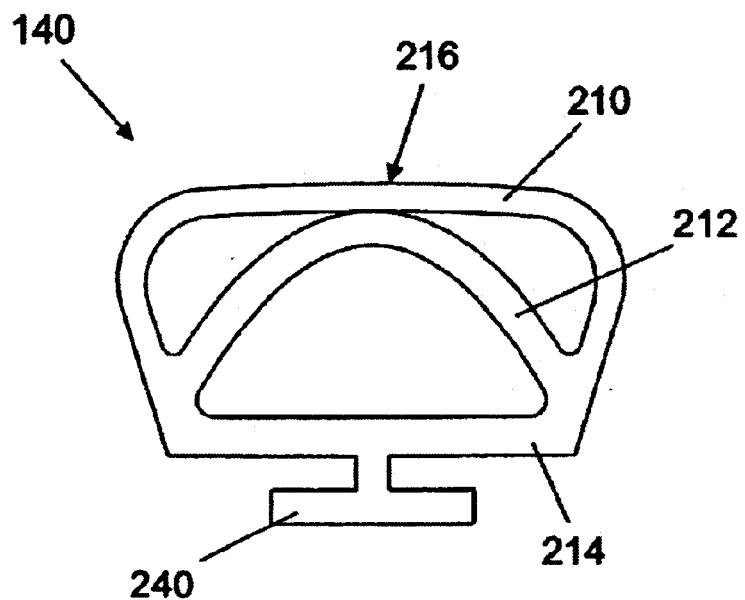
FIG. 8A shows a section view of the forehead rest cushion of FIG. 8 in its first mode of deformation.
Figure 8B:
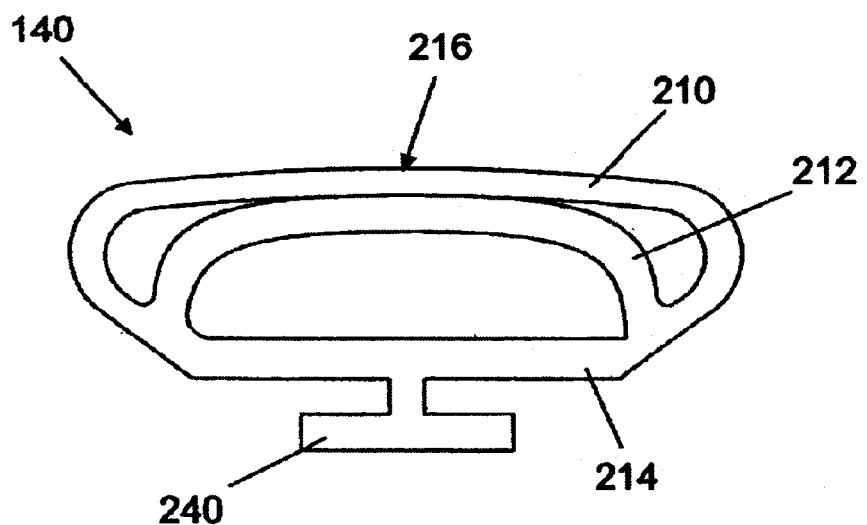
FIG. 8B shows a section view of the forehead rest cushion of FIG. 8 in its second mode of deformation.

Referring now to FIGS. 8 & 9 one embodiment of the forehead rest cushion 140 is illustrated. The cushion 140 in cross section generally includes a outer curved member 210 and a inner curved member 212 both of which are attached at each end to a straight base member 214. Both of these members may be interchangeably referred to as curved, concave or curved. The inner curved member 212 may be of a substantially similar curved shape to the outer curved member 210. The inner member 212 and outer member 210 may be coterminous, the inner member may attach to the outer member 210 or both may attach to the base 214 separately.

In this fashion when the cushion 140 comes into contact with the users face the outer curved member 210 deforms as more pressure is applied to the cushion towards the face. This comprises of the first mode of deformation. Once the outer curved member 210 deforms enough to contact the inner curved member a second mode of deformation occurs.

As will be appreciated if the outer curved member is flatter than the second curved member 212 the first mode requires less force. The relative curvature and thickness of each can be varied to give a characteristic first mode and second mode. Once in the second mode of deformation extra force is required to deform both the first curved member 210 and the second curved member 212. This configuration described above results in more even deformation force across the load bearing surface of the cushion 216 and also results in a more progressive force of cushioning when the cushion 120 is deformed.

In a further embodiment shown in FIGS. 10 and 11 the forehead rest cushion 140 is shown with a outer curved member 220 attached at either end to a straight base member 222. A inner inverted curved member 224 is inverted with respect the outer curved member 220 and is attached at either end two points on the 226, 228 on the outer curved member 220. The inner inverted curved member is lower in overall height than the outer curved member 220 such that a first mode of deformation occurs when the outer curved member 220 is deformed. A second mode of deformation occurs when the inner inverted curved member 224 contacts the base member 222. The outer curved member 220 and the inner inverted curved member 224 deform simultaneously. The forces across the load bearing surface 230 are further distributed by virtue of a generally quadrilateral member 232 including as one side the base member 222 which attaches over the inner inverted curved member 220 approximately at its ends and at its load bearing point 234. The quadrilateral member 232 provides additional stiffness and reduces lateral deformation.

In a further variation the inner inverted convex member 224 may simply attach to the underside of the outer convex member 220.

In either embodiment where included the base member includes a flange 240 which engages with a slot 2138 in the forehead rest 106 to lock the forehead rest cushion in place. The flange 240 first slides through aperture 2139 as seen in FIG. 12.

In either embodiment it will be appreciated that the base member is not necessarily required and instead each end of the curved members may engage directly with the forehead rest. The desired modes of deformation may be achieved by nesting members within each other independent of a base or other stabilising members.

What is claimed is:

1. A device for delivering a supply of gases to a user comprising:
   a patient interface, in use in fluid communication with said supply of gases,
   a forehead rest engaging said interface including a deformable resilient member configured to in use rest against the face of a user, said deformable resilient member including a first curved portion and a second curved portion, where there is a space between at least part of each of said first and second portions, wherein said deformable resilient member is capable of being deformed by a downward force on said resilient member and is configured to provide at least a first mode of deformation and a second mode of deformation, wherein the force required to deform in said first mode is less than that required to deform in said second mode and wherein said first mode of deformation comprises said first curved portion deforming and said second mode of deformation comprises the deforming of both said first curved portion and said second curved portion.

2. A device as claimed in claim 1 wherein said deformable resilient member includes a load bearing surface adapted to provide a substantially even deforming force.

3. A device as claimed in claim 1 wherein said second curved portion is nested within, and similar in shape to said first curved portion.

4. A device as claimed in claim 3 wherein said second curved portion is smaller in cross section than said first curved portion, where each of said first and second curved portions has a first and second end and either or both of said first and second curved portions are attached at each of said first and second end to a base member.

5. A device as claimed in claim 3 wherein first curved portion is attached at both ends to a base member and said second curved portion is inverted and attached at each end to, and smaller in height than, said first curved portion; said second mode of deformation begins where said second curved portion is in contact with said base member and both said first curved portion and said second bridge member simultaneously deform.

6. A device as claimed in claim 5 wherein said first curved portion further comprises further members attaching to the said second curved portion at least three points to form an outer cross section substantially quadrilateral in cross section.

7. A device as claimed in claim 1 wherein said deformable resilient member is moulded from silicon.

8. A device as claimed in claim 1 wherein said deformable resilient member is extruded from silicon.

* * * * *

UNITED STATES PATENT AND TRADEMARK OFFICE
CERTIFICATE OF CORRECTION

PATENT NO.   : 6,832,610 B2
DATED        : December 21, 2004
INVENTOR(S)  : Lewis George Gradon et al.

It is certified that error appears in the above-identified patent and that said Letters Patent is hereby corrected as shown below:

<u>Column 4,</u>
Lines 31-32, "1108 to adapt" should read -- (not shown, but similar to the headgear 108 shown in Figure 2) --
Line 54, "bead 158" should read -- bead 1158 --

Signed and Sealed this

Tenth Day of May, 2005

JON W. DUDAS
*Director of the United States Patent and Trademark Office*